United States Patent [19]

Lang et al.

[11] Patent Number: 5,304,310
[45] Date of Patent: Apr. 19, 1994

[54] METHOD FOR CONCENTRATING AND PURIFYING HIRUDIN FROM LEECHES

[75] Inventors: Kurt Lang, Penzberg; Andreas Kreimeyer, Roemerberg, both of Fed. Rep. of Germany

[73] Assignee: BASF Aktiengesellschaft, Ludwigshafen, Fed. Rep. of Germany

[21] Appl. No.: 910,320

[22] PCT Filed: Dec. 20, 1990

[86] PCT No.: PCT/EP91/02269
§ 371 Date: Jul. 17, 1992
§ 102(e) Date: Jul. 17, 1992

[87] PCT Pub. No.: WO91/10677
PCT Pub. Date: Jul. 25, 1991

[30] Foreign Application Priority Data

Jan. 18, 1990 [DE] Fed. Rep. of Germany ....... 4001238

[51] Int. Cl.$^5$ ...................... B01D 11/02; A61K 35/62
[52] U.S. Cl. .................... 210/639; 424/550; 514/21; 530/344; 530/855
[58] Field of Search ........ 210/739, 634, 639; 435/188; 436/178, 179; 424/94.64, 537, 550, 551; 514/12, 21; 530/344, 855, 858

[56] References Cited

U.S. PATENT DOCUMENTS

| | | |
|---|---|---|
| 3,300,383 | 1/1967 | Markwardt et al. ................... 514/21 |
| 3,432,596 | 3/1969 | Markwardt et al. ................ 530/344 |
| 3,637,462 | 1/1972 | Hill et al. ............................. 435/188 |
| 4,390,630 | 6/1983 | Sawyer et al. ................... 424/94.64 |
| 4,588,587 | 5/1986 | Gasic .................................... 424/550 |
| 4,791,100 | 12/1988 | Kramer et al. ....................... 514/12 |
| 4,832,849 | 5/1989 | Cardin ................................. 424/550 |
| 4,980,065 | 12/1990 | Hsu ...................................... 210/634 |
| 5,078,886 | 1/1992 | Hsu ...................................... 210/634 |
| 5,182,113 | 1/1993 | Rigbi et al. .......................... 424/537 |

FOREIGN PATENT DOCUMENTS 245985 11/1987 European Pat. Off. ............ 210/639

OTHER PUBLICATIONS

Hackh's Chemical Dictionary, Fourth Edition, Julius Grax, Published 1969 by McGraw-Hill, Inc.
Bioseparations, "Downstream Processing for Biotechnology", 1988, Paul A. Belter, pp. 100-111.
Green, A. A. & Hughes, W. L., Protein Fractionation on the Basis of Solubility in Aqueous Solutions of Salts and Organic Solvents, Methods in Enz. I, 67-90 (1955).
Schüguri, K. Reactive extraction in biotechnology. Separations for Biotechnology Eds. Verral. M. S. & Hudson, M. J. pp. 260-269 (1987).
Johansson, G. Partitioning of Proteins In Partitioning in Aqueous Two-Phase Systems pp. 161-225 (1985).
Albertsson, P. A. Partition of Proteins in Liquid Polymer-Polymer Two Phase Systems Nature 152:709 (1958).

*Primary Examiner*—Joseph W. Drodge
*Attorney, Agent, or Firm*—Keil & Weinkaup

[57] ABSTRACT

A method for the concentration and purification of biomolecules is described and comprises introducing the biomolecule into an aqueous/organic solvent system and bringing about a phase separation by addition of salts, where the pH at which the concentration takes place, the solvents suitable for the aqueous/organic solvent system, and the nature of the salt are determined in a series of tests one embodiment concerns concentration of hirudin by using propanol, butanol or acetone a the solvent and sodium chloride as the salt.

2 Claims, No Drawings

METHOD FOR CONCENTRATING AND PURIFYING HIRUDIN FROM LEECHES

DESCRIPTION

Efficient and economic purification methods play a central part in the preparation of chemical and biological products. During the course of the development of biotechnology and genetic engineering in recent years increasing importance has become attached, in particular, to the development of methods for purifying proteins, peptides and vitamins on the industrial scale.

An important step in the isolation of most cellular constituents is the fractionation of the starting material or of an intermediate during the course of the purification. Used for this purpose are, as a rule, (fractional) precipitations or partition chromatographies. To carry out precipitations, the properties of the solvent are altered in such a way, by adding appropriate reagents, that the solubility of the protein greatly decreases and it precipitates. The solubility can be altered by adding salts such as ammonium sulfate or organic solvents such as ethanol or by changing the pH or the temperature (Green, A. A. & Hughes W. L. in "Methods in Enzymology", volume I, pp. 67–90 (1955); Belter et al, 1988, pages 100 ff. in "Bioseparations", eds.: Belter, P. A., Cussler, E. L. & Hu, W. -S.).

Liquid-liquid two-phase partition chromatographies have also been employed for a long time for purifying biomolecules. In the 1940s and 1950s, exclusively organic/aqueous two-phase systems containing water-immiscible organic solvents were used. Although these are very suitable for concentrating and purifying low molecular weight biomolecules such as antibiotics and vitamins (Schlügerl, K., 1987, in "Separations for Biotechnology", eds.: Verral, M. S. & Hudson, M. J. pp. 260-269), there are strict limits on their use for isolating proteins in particular. In particular, the denaturation and precipitation of the proteins in the organic/aqueous system preparer (sic) great problems (Johansson G., 1985, in "Partitioning in aqueous two-phase systems", Acad. Press, pp. 161-225).

Another method for liquid-liquid two-phase extraction was developed by Albertson in the late 1950s. He used 2-phase systems with two aqueous phases and was able to show that these are very suitable for, in particular, the concentration of proteins (Nature 182, 709 (1958)). Since then, almost exclusively aqueous 2-phase systems have been used and further developed for the extraction of proteins with 2-phase systems. However, because of the high costs of starting materials for phase-induced polymers such as polyethylene glycol or dextran, aqueous 2-phase extractions are carried out only rarely on the industrial scale.

The invention relates to a method for concentrating and purifying biomolecules, which comprises dissolving the biomolecule in a mixture of water and/or of a buffer and of a water-miscible organic solvent, and concentrating it in one of the phases which separate in the subsequent phase separation brought about by the addition of salts, where the pH at which the concentration takes place, the solvents suitable for the extraction of the biomolecule, and the nature of the salt are determined in a series of tests.

Suitable biomolecules are, in particular, vitamins and, preferably, proteins and peptides. To carry out the method, the biomolecule is first introduced into water or a buffer and/or directly into an aqueous/organic solvent system.

Care must be taken when the organic solvent is added to the aqueous phase that the protein to be purified remains in solution. If the protein does not remain in solution, it is advisable to alter the pH, the temperature, the proportion and nature of the organic solvent, the nature of the buffer and its concentration, the protein concentration and the nature and concentration of the salt. If another substance precipitates on addition of the organic solvent, it is removed by centrifugation or filtration. Particularly suitable solvents are 1- and 2-propanol, acetone, THF and acetonitrile. Most suitable for purifying hirudin are n-butanol and 2-propanol.

The salt is added to the solution obtained in this way for the phase separation. Examples of suitable salts are alkali metal chlorides- such as lithium, sodium, potassium or cesium chloride-, calcium chloride, manganese(II) chloride, ammonium sulfate, ammonium nitrite, magnesium sulfate, sodium formate, sodium acetate, sodium citrate, potassium sodium tartrate and potassium carbonate. It is also possible to use, for example, D-sorbitol in place of a salt. The most suitable salt is again determined in a preliminary test. The same applies to the amount of salt. As a rule, the phase separation is best when the amount of salt added is such that the phases are saturated with the salt.

Particularly suitable for purifying hirudin are sodium chloride and ammonium sulfate. Care must also be taken, in the choice of the correct parameters, that the protein after the phase separation is very predominantly present in the aqueous phase. No general rule can be given for the choice of the parameters, and it is advisable to determine the parameters in a few preliminary tests.

If a precipitate appears on phase separation, it is discarded.

The protein is isolated from the aqueous phase in a known manner, for example by hydrophobic chromatography or precipitation. It can also be subjected to further purification steps.

The method according to the invention is rapid, economic and easy to carry out. It is distinguished from previous organic/aqueous extractions in that the protein to be purified remains dissolved in the mixed organic/aqueous phase and is only transferred by the subsequent phase separation preferably into the aqueous phase which separates out. A particular advantage of the novel method is that the proteins are continuously in an aqueous medium because of the use of water-miscible organic solvents. Thus, under suitable conditions, many proteins can be concentrated in active form.

However, the method can also be used for concentrating inactive or denatured proteins.

EXAMPLE 1

Organic/Aqueous Partition Chromatography with Hirudin-containing Cell Extract

The starting material was an E. coli cell extract which had undergone preliminary purification and which, besides hirudin, still contained numerous extraneous proteins, peptides and constituents, some of them colored, of the fermentation medium and of the cells. The hirudin had been concentrated to about 10% (based on protein).

An aqueous solution of this extract with a protein concentration of 10-100 mg/ml was mixed at 0°-20° C.

with 1 volume of i-propanol, and the pH of the mixed phase was adjusted to pH 1-2 with 2N HCl. Precipitated material was removed by centrifugation (30 min, 10000 g, 0°-20° C.) or filtration. The supernatant or the filtrate was then adjusted to pH 4-4.3 with 2N NaOH and, while stirring, solid NaCl was added to saturation. After completion of the stirring process, spontaneous separation of the organic and aqueous phases started. At the same time, a thick solid interphase predominantly composed of precipitated proteins formed between the organic and the aqueous phase. The hirudin was almost entirely located in the aqueous phase. The yield of active hirudin in the aqueous phase was 70-90%. A further increase in the yield is possible if the organic phase is repeatedly extracted with $H_2O$/sodium chloride.

The extraction resulted in the hirudin being concentrated by a factor of at least 5. In addition, hydrophobic impurities (sic) (some of them colored) were transferred into the i-propanol phase which, after the phase separation, had a very dark color.

EXAMPLE 2

Organic/Aqueous Partition Chromatography with a Protein A-Hirudin Fusion Protein which had Undergone Preliminary Concentration The starting material used was the precipitate from the precipitation of an E. coli cell disruption. It received (sic) inactive hirudin in the form of a fusion protein with the N-terminal region of protein A from Staphylococcus aureus. The protein portion of the fusion protein in the total protein was about 40%. Besides extraneous proteins, the precipitate contained large amounts of cell and fermentation constituents.

The precipitate was taken up in water at a concentration of 50 g of precipitate/1 l. The pH of the solution was adjusted to pH 5 with 40% strength $H_2SO_4$ or 2N NaOH. Then 1 volume of i-propanol was added and the pH of the mixed phase was again adjusted to pH 5, and insoluble material was removed by centrifugation (10000 g, 15 min, 20° C.). The pH of the supernatant was now adjusted to pH 7 with 2N NaOH. After this, solid NaCl was added to the supernatant, while stirring, to a concentration of 1.5M NaCl. After completion of the stirring process, spontaneous separation of the organic and aqueous phase took place, with formation between these of an interphase composed predominantly of denatured proteins.

The protein A-hirudin fusion protein was located almost quantitatively in the aqueous phase. The proportion of fusion protein in the total protein in the aqueous phase was about 80%. Besides extraneous protein, the extraction greatly reduced the concentration of, in particular, DNA and constituents of the fermentation medium and cell components which are hydrophobic and sparingly soluble under the extraction conditions. This greatly simplified the further processing of the fusion protein.

It is also possible to concentrate the protein A-hirudin fusion protein in the organic phase. This is achieved by carrying out the phase separation not as described above, at pH 7, but at pH 1.5. The pH is adjusted with 2N HCl before the addition of salt.

The protein A-hirudin fusion protein which had undergone preliminary concentration was obtained as follows:

Preparation of the Expression Plasmid a) Construction of the Vector

The protein A vector pRIT 2T (FIG. 1) is commercially available and has been described in detail (Pharmacia order no. 27-4808-01).

This vector was modified as follows: It was cleaved with the restriction endonuclease Hind III. The larger fragment (vector) was isolated from an agarose gel by electroelution. The complementary oligonucleotides Koe 1/2 (sequence 1) were ligated into this vector. The resulting chimeric plasmid was transformed into the lambda lysogen strain N 4830-1 (Pharmacia order no. 27-4808-01). The clone with the correct orientation of the oligonucleotides was screened out of the possible recombinants by means of Hind III/EcoRI restriction mapping and was checked by DNA sequencing. This expression plasmid was called pRIT 2TA.

b) Insertion of a Synthetic Hirudin Gene With Adapter

The pRIT 2TA DNA was cut with EcoRI and SalI, and the larger DNA fragment (a) was isolated from an agarose gel by electroelution.

A synthetic hirudin gene (sequence 6) was prepared using a DNA synthesizer (Applied Biosystems, model 380A). For this, 4 oligonucleotides (Koe 3-Koe 6) were prepared (sequences 2-5). The oligonucleotides were kinased and ligated with EcoRI/SalI linearized plasmid pUC 18. The construction was checked by DNA sequencing. The hirudin gene (b) including the adapter was cut out of this chimeric plasmid (pUC 18-Hir) with EcoRI, and isolated by agarose gel electrophoresis and electroelution. The synthetic hirudin gene contains, besides two stop codons at the 3' end and the SalI recognition site, an adapter sequence which links the hirudin gene, with retention of the reading frame, to the protein A fusion partner via the EcoRI cleavage site.

The isolated DNA fragments a and b were ligated together and transformed into the lysogenic strain N 4830-1. This resulted in the protein A-hirudin expression vector pRIT2TA-Hir (FIG. 2).

Expression of the fusion protein

The expression plasmid pRIT 2TA-Hir was transformed into the strain E. coli N 4830-1 (Pharmacia order no. 27-4808-01). This strain contains the thermosensitive lambda repressor CI 857 chromosomally.

100 ml of MIM medium (MIM=32 g of tryptone, 20 g of yeast extract, 6 g of $Na_2HPO_4$, 3 g of $KH_2PO_4$, 0.5 g of NaCl, 1 g of $NH_4Cl$ per liter and 0.1 mM $MgSO_4$ plus 0.001 mM $FeCl_3$) were sterilized in a 1 l Erlenmeyer flask with baffles, and ampicillin was added (ad 100 μg/ml). The medium was inoculated with 1 ml of a fresh overnight culture of the strain pRIT 2TA-Hir/N 4830-1 and incubated at 28° C. with shaking until the absorption at 550 nm was 0.6. Then 100 ml of fresh MIM/amp medium at 65° C. were added, and incubation was continued at 42° C. for 4 h. The required fusion protein was synthesized during this time. The cell wall was removed enzymatically by adding lysozyme to 75 mg/l and incubation (3 h, 37° C.). It was then possible to disrupt the cells mechanically (Manton-Gaulin press, freezing cycle, vigorous stirring), by a heat shock to 80° C. or a hypotonic lysis, and to liberate the soluble fusion protein into the medium.

EXAMPLE 3

Organic/aqueous partition chromatography with hirudin and various phase systems The starting material for the partition chromatographies with hirudin with various solution systems and salts was an aqueous hirudin solution of concentration 1 mg/ml in 20 mM sodium acetate, pH 4.0.

It was possible to concentrate the hirudin very predominantly in the aqueous phase using several combinations of various solvents and salts (cf. Tab. 1).

The chymotrypsin solution was divided into aliquots each of 5 ml, and 1 volume of the various organic solvents (see Tab. 2) was added to and mixed with the mixtures. NaCl or D-sorbitol (see Tab. 3) was added to the mixed phases to saturation at room temperature (20° C.) with stirring. After completion of the stirring process, phase separation started spontaneously. Tab. 3 shows the volumes of the predominantly aqueous lower phase, the volumes of the predominantly organic upper phase and the activities found in these phases.

The chymotrypsin activity was determined using the

TABLE 1

Organic/aqueous partition chromatography with hirudin in various solvent systems and salts

| Nature of salt | Solvent system (v/v = 50/50) | Volume proportion after phase separation (%) | | Activity distribution after phase separation % | |
|---|---|---|---|---|---|
| | | lower phase ($H_2O$) | upper organ. phase | lower phase ($H_2O$) | upper organ. phase |
| NaCl | 2-Propanol/$H_2O$ | 48 | 52 | >90 | <10 |
| | Acetone/$H_2O$ | 75 | 25 | >90 | <10 |
| | Acetonitrile/$H_2O$ | 58 | 42 | >90 | <10 |
| | THF*/$H_2O$ | 40 | 60 | >80 | <10 |
| | 1-Propanol/$H_2O$ | 48 | 52 | >80 | <10 |
| $(NH_4)_2SO_4$ | 2-Propanol/$H_2O$ | 40 | 60 | >60 | <40 |
| | Acetone/$H_2O$ | 30 | 70 | >80 | <10 |
| | Acetonitrile/$H_2O$ | 40 | 60 | >80 | <10 |
| | THF*/$H_2O$ | 40 | 60 | >50 | <10 |
| | 1-Propanol/$H_2O$ | 40 | 60 | >80 | <10 |

*THF = tetrahydrofuran

TABLE 2

Organic/aqueous partition chromatography with hirudin in various solvent systems and salts

| Nature of salt | Solvent system (v/v = 50/50) | Volume proportion after phase separation (%) | | Activity distribution after phase separation % | |
|---|---|---|---|---|---|
| | | lower phase ($H_2O$) | upper organ. phase | lower phase ($H_2O$) | upper organ. phase |
| $NH_4NO_3$ | 2-Propanol/$H_2O$ | 70 | 30 | >60 | — |
| $(NH_4)_2SO_4$ | " | 40 | 60 | 60 | 40 |
| CsCl | " | 60 | 40 | >80 | 40 |
| $CaCl_2$ | " | 60 | 40 | >30 | — |
| K Na tartrate | " | 20 | 80 | >40 | — |
| LiCl | " | 60 | 40 | not determined | — |
| $MnCl_2$ | " | 60 | 40 | >80 | — |
| $MgSO_4$ | " | 30 | 70 | not determined | — |
| $CH_3COONa$ | " | 80 | 20 | >70 | — |
| NaCl | " | 48 | 52 | >90 | <10 |
| Na citrate | " | 20 | 80 | >40 | — |
| $K_2CO_3$ | " | 50 | 50 | not determined | — |

EXAMPLE 4

Organic/aqueous partition chromatography with chymotrypsin $A_4$ and various phase systems The starting material used for the partition chromatographies was an aqueous chymotrypsin solution of concentration 1 mg/ml.

conversion of the substrate peptide N-succinyl-Ala-Ala-Pro-Phe-p-nitroaniline (Anal. Biochem. 99, 316 (1979)).

TABLE 3

Organic/aqueous partition chromatography with chymotrypsin in various solvent systems and salts

| Nature of salt | Solvent system (v/v = 1/1) | Volume proportion after phase separation (%) | | Activity distribution after phase separation % | |
|---|---|---|---|---|---|
| | | lower phase ($H_2O$) | upper organ. phase | lower phase ($H_2O$) | upper organ. phase |
| NaCl | n-Propanol/$H_2O$ | 50 | 50 | >80 | — |
| | i-Propanol/$H_2O$ | 50 | 50 | >80 | — |
| | Acetonitrile/$H_2O$ | 60 | 40 | >40 | — |
| D-sorbitol | i-Propanol/$H_2O$ | 30 | 70 | >80 | — |

EXAMPLE 5

Organic/aqueous partition chromatography with folic acid in various phase systems The starting material for the partition chromatographies was an aqueous folic acid solution of concentration 0.1 mg/ml in 20 mM sodium phosphate pH 7.0. 5 ml samples of the folic acid solution were each mixed with 5 ml of the water-miscible organic solvent (see Tab. 4) at room temperature (20° C.). For the subsequent separation of the solvents into the aqueous and organic phase, various salts (see Tab. 4) were added to saturation while stirring. The phase separation took place spontaneously after completion of the stirring process.

The volumes of the aqueous and organic phases after the phase separation and the proportions of folic acid contained therein are shown in Tab. 4. The amounts of folic acid contained in the various phases were determined by spectroscopy. For this, the absorption of the phases at 346 nm was measured. The content of folic acid in the phases was calculated, taking account of the different volumes, by means of the absorption of a folic acid solution of known concentration (0.1 mg/ml in 20 mM sodium phosphate, pH 7.0) at 346 nm.

The folic acid can be concentrated almost quantitatively in the aqueous phase with a large number of the solvent systems used. However, some systems (e.g. isopropanol/$H_2O$/lithium chloride) also allow concentration in the organic phase.

TABLE 4

Organic/aqueous partition chromatography with folic acid in various solvent systems and salts

| Nature of salt | Solvent system (v/v = 1/1) | Volume proportion after phase separation (%) | | Folic acid distribution after phase separation % | |
|---|---|---|---|---|---|
| | | lower phase ($H_2O$) | upper organ. phase | lower phase ($H_2O$) | upper organ. phase |
| $(NH_4)_2SO_4$ | Acetone/$H_2O$ | 30 | 70 | <40 | >60 |
| " | Acetonitrile/$H_2O$ | 45 | 55 | >80 | <20 |
| " | Isopropanol/$H_2O$ | 35 | 65 | >80 | <20 |
| " | 1-Propanol/$H_2O$ | 35 | 65 | >60 | <40 |
| " | Tetrahydrofuran/$H_2O$ | 70 | 30 | >60 | <40 |
| NaCl | Acetone/$H_2O$ | 30 | 60 | >60 | <40 |
| " | Acetonitrile/$H_2O$ | 60 | 40 | >80 | <20 |
| " | Isopropanol/$H_2O$ | 45 | 55 | >80 | <20 |
| " | 1-Propanol/$H_2O$ | 45 | 55 | >80 | <20 |
| " | Tetrahydrofuran/$H_2O$ | 45 | 55 | >70 | <30 |
| Ammonium nitrate | Isopropanol/$H_2O$ | 60 | 40 | >80 | <20 |
| Calcium chloride | " | 50 | 50 | >70 | <30 |
| Cesium chloride | " | 60 | 40 | >80 | <20 |
| Potassium carbonate | " | 45 | 55 | >70 | <30 |
| Potassium sodium tartrate | " | 20 | 80 | <40 | >60 |
| Lithium chloride | " | 40 | 60 | <30 | >70 |
| Magnesium sulfate | " | 20 | 80 | <40 | >60 |
| Sodium acetate | " | 55 | 45 | >80 | <20 |
| Sodium citrate | " | 20 | 80 | <40 | >60 |
| Sodium formate | " | 50 | 50 | >80 | <20 |

We claim:

1. A method of concentrating a hirudin-containing mixture which comprises: forming a solution of the hirudin-containing mixture in a mixture of water and a solvent selected from the group consisting of 1-propanol, 2-propanol, n-butanol and acetone and mixtures thereof; adjusting the pH of the solution to from about 4.0 to 7.0; adding sodium chloride to the solution to form separate phases, one being an aqueous phase containing the hirudin, and separating off the aqueous phase containing hirudin.

2. A method of concentrating a hirudin-containing mixture which comprises: forming a solution of the hirudin-containing mixture in a mixture of water and a solvent selected from the group consisting of 1-propanol, 2-propanol, n-butanol and acetone and mixtures thereof; adjusting the pH of the solution to from about 4.0 to 4.3; adding sodium chloride to the solution to form separate phases, one being an aqueous phase containing the hirudin, and separating off the aqueous phase containing hirudin.

* * * * *